United States Patent [19]

Morimoto et al.

[11] 4,065,619
[45] Dec. 27, 1977

[54] 7-(α-SULFOACYLAMIDO)CEPHALOSPORINS

[75] Inventors: Shiro Morimoto, Kobe; Hiroaki Nomura, Takatsuki; Takeshi Fugono, Kawanishi; Isao Minami, Osaka, all of Japan

[73] Assignee: Takeda Chemical Industries, Ltd., Japan

[21] Appl. No.: 719,704

[22] Filed: Sept. 2, 1976

Related U.S. Application Data

[63] Continuation of Ser. No. 552,752, Feb. 25, 1975, abandoned, which is a continuation of Ser. No. 272,637, July 17, 1972, abandoned.

[30] Foreign Application Priority Data

July 17, 1971  Japan .................................. 46-53466
Oct. 22, 1971  Japan .................................. 46-84130

[51] Int. Cl.² ............... C07D 501/44; C07D 501/46; A61K 31/545
[52] U.S. Cl. ..................... 544/25; 424/246; 544/24
[58] Field of Search ...................... 260/243 C

[56] References Cited

U.S. PATENT DOCUMENTS 3,338,897  8/1967  Takano et al. .................. 260/243 C
3,382,238  5/1968  Dolfini ........................... 260/239.1
3,988,327  10/1976  Ishiguro et al. ................. 260/243 C

FOREIGN PATENT DOCUMENTS 1,310,642  3/1973  United Kingdom ............ 260/243 C Primary Examiner—Nicholas S. Rizzo
Assistant Examiner—Diana G. Rivers
Attorney, Agent, or Firm—Craig & Antonelli

[57] ABSTRACT

Novel cephalosporins of the formula,

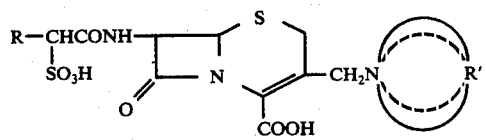

wherein R is a hydrogen atom or an alkyl, aryl or thienyl group, and R' is a group which constitutes together with the adjacent nitrogen atom a 5- or 6-membered ring containing 1 or 2 nitrogen atoms, which are effective particularly against *Pseudomonas aeruginosa* as well as against other Gram negative and positive microorganisms, for example, N-[7-(α-sulfophenylacetamido)-ceph-3-em-3-ylmethyl] pyridinium 4-carboxylate, N-[7-(α-sulfo-3'-thienylacetamido)ceph-3-em-3-ylmethyl] pyridinium-4-carboxylate, and their pharmaceutically acceptable salts thereof. Sodium salt of the former is prepared by, e.g. reacting sodium 7-(α-sulfophenylacetamido) cephalosporanate with pyridine in water.

6 Claims, No Drawings

7-(α-SULFOACYLAMIDO)CEPHALOSPORINS

This is a continuation of application Ser. No. 552,752 filed Feb. 25, 1975, which is a continuation of Ser. No. 272,637 filed July 17, 1972, each now abandoned.

This invention relates to novel cephalosporins and preparation thereof. More particularly, the invention pertains to cephalosporins of the formula,

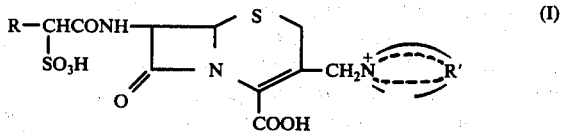

wherein R is a hydrogen or an alkyl, aryl or thienyl group; and R' is a group which constitutes, together with the adjacent nitrogen atom, a 5- or 6-membered ring containing 1 or 2 nitrogen atoms, and to a process for preparing the same.

Ever since the discovery of cephalosporin C, there have been developed various derivatives of cephalosporin type antibiotics which have been substituted at the 7- and 3-positions. However, compounds which are effective at practical concentrations against *Pseudomonas aeruginosa* have not been reported yet.

The present inventors have found the fact that the novel cephalosporins represented by the aforesaid formula (I) are not only effective for the therapy of various infectious diseases derived from Gram-positive and Gram-negative pathogenic bacteria but also show marked activities at low concentrations against *Pseudomonas aeruginosa*. In the cephalosporins (I) of the present invention, sulfonic acid groups in the substituents at the 7-positions have been bonded directly to asymmetric carbons. It should therefore be understood that the cephalosporins of the present invention include D-type, L-type and DL-type cephalosporin compounds.

The cephalosporins (I) of the present invention can be prepared by converting the 5-amino-5-carboxyvaleryl group at the 7-position of cephalosporin C to the desired α-sulfoacyl group and by converting the acetoxy group at the 7-position to the nitrogen-containing heterocyclic group. Either conversion at the 3- or 7-position may be conducted at first, followed by the conversion of the other position.

A. Procedures for first conducting the conversion at the 7-position and then at the 3-position:

7-Aminocephalosporanic acid (hereinafter referred to as "7-ACA") is allowed to react with an α-sulfocarboxylic acid of the formula,

or with a functional derivative thereof, whereby a sulfocephalosporanic acid of the formula,

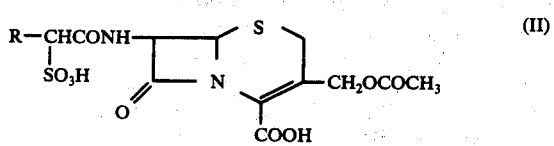

can be obtained (Belgian Pat. No. 762,725). When a compound representable by the general formula (II) is subjected to the subsequent reaction, it is desirably in such a form that R in the formula is a hydrogen atom; an alkyl group such as a methyl, ethyl, isopropyl, butyl, cyclohexyl or dodecyl group; or an aryl group such as a phenyl, nitrophenyl, aminophenyl, tolyl, naphthyl, or thienyl group. Further, so far as no detrimental effect is brought about in the subsequent 3-position conversion reaction, the carboxyl group at the 4-position and/or the sulfo group on the side chain thereof may form a salt with, for example, sodium, potassium, magnesium, calcium, aluminum or triethylamine. In some cases, the carboxyl group at the 4-position may be a group which is easily removable, for example, a benzyl oxycarbonyl, β-methylsulfonylethyl oxycarbonyl, benzhydryl oxycarbonyl or trimethylsilyl oxycarbonyl group.

Subsequently, the sulfocephalosporanic acid (II) is allowed to react with a nitrogen-containing heterocyclic compound of the formula,

which is a 5- or 6-membered ring compound containing 1 or 2 nitrogen atoms and which contains at least 1 double bond in the ring. Desirably, the ring is an aromatic one. The nitrogen-containing heterocyclic compound (III) may be a condensed ring which commonly has 2 adjacent carbon atoms in the rings. These rings may have as a substituent an alkyl group such as a methyl or ethyl group; an amino, carboxyl, carbamoyl, hydrazinocarbonyl, sulfo, carbinol or aldehyde group; or a halogen such as bromine or chlorine. Examples of said nitrogen-containing heterocyclic compound (III) include pyridine derivatives such as quinoline; picoline; nicotinic acid; nicotinic acid amide; isonicotinic acid amide; isonicotinic acid hydrazide; pyridine derivatives such as, for example, m-bromopyridine, pyridinesulfonic acid, pyridine-m-carbinol (3-hydroxymethylpyridine), pyridinealdehyde and isoquinoline; pyrazine; pyrazinic acid amide (2-carbamoylpyrazine); pyridazine; pyrimidine; imidazole and 1-methylimidazole.

The reaction of the sulfocephalosporanic acid (II) with the nitrogen-containing heterocyclic compound (III) is effected according to a procedure known per se. Generally, it is advantageous to carry out the reaction in water or a solvent strong in polarity. The reaction is conducted around neutral pH, preferably pH 5 to 8. Ordinarily, the nitrogen-containing compound is used in a proportion of about 1 to 10 moles per mole of the sulfocephalosporanic acid. Further, the reaction may be conducted in the presence of a catalyst such as isocyanate, thioisocyanate or thiol compounds in a proportion of about 1 to 40 moles, preferably about 5–20 moles, per mole of the sulfocephalosporanic acid (II), whereby the end product can be obtained in a high yield. The above-mentioned catalyst is once introduced into the 3-position of the sulfocephalosporanic acid to lead the latter into a functional derivative. This functional derivative is isolated or not isolated, and allowed to react with the nitrogen-containing heterocyclic compound (III). The reaction temperature and time vary depending on the kind of reaction reagent and on the kind of the solvent used. In most cases, however, the reaction is effected at a temperature ranging from room temperature to 100° C, preferably 40° to 70° C, for 1 to 48 hours. The thus obtained reaction product (I) is purified and recovered according to a known means, e.g. solvent extraction, concentration, chromatography, freeze-drying and recrystallization.

B. Procedures for first conducting the conversion at the 3-position and then at the 7-position:

The conversion of acetoxy group at the 3-position of cephalosporin C can be effected according to the process disclosed in, for example, U.S. Pat. Nos. 3,225,038 or 3,217,000 or German Pat. No. 1,817,121. The resulting cephalosporin having the nitrogen-containing heterocyclic group at the 3-position can be easily converted, according to the process disclosed in, for example, Dutch Pat. No. 6,401,421, British patent specification No. 1,041,985 or U.S. Pat. No. 3,575,970, into a corresonding aminocephalosporanic acid derivative of the formula,

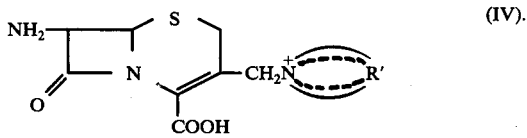

(IV).

Alternatively, the aminocephalosporanic acid derivative (IV) may be prepared by deacylating cephalosporin C and then substituting the 3-position of the resulting 7-ACA. It is needless to say that the aminocephalosporanic acid derivative (IV) may be in any of such forms as salts and esters, like in the case of the aforesaid sulfocephalosporanic acid (II).

The reaction of the aminocephalosporanic acid derivative (IV) with the α-sulfocarboxylic acid (V) or a functional derivative thereof may also be accomplished according to a procedure known per se. In case the α-sulfocarboxylic acid (V) is used in a free form, it is preferable to carry out the reaction in the presence of a condensing agent. The condensing agent is, for example, an N,N'-di-substituted carbodiimide, e.g. N,N'-dicyclohexylcarbodiimide; an azolide compound, e.g. N,N'-thionylimidazole; N-ethoxycarbonyl-2-ethoxy-1,2-dihydroquinoline, phosphorus oxychloride or alkoxyacetylene. As the reactive ester of the acid (V), there is used any of carboxylic acid halides, anhydrides, azides and active esters. The above acylation reaction proceeds advantageously and smoothly in a solvent. As the solvent, such a conventional solvent as, for example, water, acetone, tetrahydrofuran, dioxane, acetonitrile, chloroform, dichloromethane, dichloroethylene, pyridine, dimethylaniline, dimethylformamide, dimethylacetamide or dimethyl sulfoxide is conveniently used. The reaction temperature is not particularly limited. Ordinarily, however, the reaction is effected under cooling or at room temperature. The reaction product can be purified and recovered, utilizing the properties of the end product cephalosporin (I), according to, for example, column chromatography, extraction, isoelectric point precipitation, countercurrent distribution or recrystallization.

The cephalosporins (I) can be put into the same uses as the conventional cephalosporins, though the uses thereof more or less vary depending on the kind of nitrogen-containing heterocyclic group at the 3-position and/or the acyl group at the 7-position. The present compounds (I) are useful as pharmaceuticals since they have strong antibacterial activities against a wide scope of pathogenic bacteria including *Pseudomonas aeruginosa*, to which the conventional cephalosporin preparations have been substantially ineffective.

The cephalosporins (I) of the present invention are generally administered in an injectable form, etc. in a similar manner to known cephalosporin preparations, but their dosages, dosage forms, etc. vary with their substituent groups at the 3-position and acyl groups at the 7-position. For example, the effective dose of sodium N-[7-(α-sulfophenylacetamido)-ceph-3-em-3-ylmethyl]-pyridinium-4-carboxylate is about 0.25 g. to 2.5 g. every 4 to 6 hours for an adult human.

The present invention is illustrated in further detail below with reference to examples, but it is to be understood that the examples are solely for the purpose of illustration and not to be construed as limitations of the invention, and that many variations may be resorted to without departing from the spirit and scope of the invention. In this specification, "g.", "mg.", "l.", "ml.", "cm.", "mm.", "kg.", "mcg.", "m.p." and "decomp." are abbreviations of "gram", "milligram", "liter", "milliliter", "centimeter", "millimeter", "kilogram", "microgram", "melting point" and "decomposed", respectively; all the temperatures are uncorrected.

EXAMPLE 1

1. Preparation of α-sulfobenzyl cephalosporin

A solution comprising 2.5 ml. of a 1N—NaOH solution and 5 ml. of water was ice-cooled to 0° to 5° C, and 680 mg. of 7-aminocephalosporanic acid was dissolved in the solution with thorough stirring. Into the resulting solution was dropped with stirring over a period of 15 minutes a solution of 585 mg. of α-sulfophenylacetic acid chloride in 7 ml. of diethyl ether. Subsequently, the aqueous layer was separated, adjusted to pH 1.5 by addition of 1N—HCl and then extracted 2 times with 15 ml. of n-butanol, and the extract was washed 2 times with 5 ml. each portion of water and extracted with a saturated aqueous $NaHCO_3$ solution. The resulting extract was adjusted to pH 6.5, washed with ether and then subjected to freeze-drying to obtain 385 mg. of the desire product in the form of sodium salt. IR $\nu_{max}^{KBr}$ (cm.$^{-1}$): 1755 (lactam, acetate), 1612 (—COO-), 1680 (—CONH—), 1225 (—$SO_2$—), 1046 (—$SO_3Na$). NMR ($D_2O$) ppm: 2.09 (3H, singlet), 3.42 (2H, quartet, $J_1$=18.0 c/s, $J_2$=18.0 c/s), 4.75 (2H), 5.09 (1H, singlet), 5.10 (1H, doublet, J=4.5 c/s), 5.70 (1H, doublet, J=4.5 c/s), 7.52 (5H, multiplet). UV $\lambda_{max}^{H_2O}$: 259 mμ (7.1 × $10^3$)

2. Preparation of sodium N-[7-(α-sulfophenylacetamido)ceph-3-em-3-ylmethyl]-pyridinium-4-carboxylate 0.355 Gram (6.9 × $10^{-4}$ mole) of 7-(α-sulfophenylacetamido)cephalosporanic acid (α-sulfobenzylcephalosporin), 0.34 g.(3.5×$10^{-3}$ mole) of potassium thiocyanate and 0.15 ml. (1.88×$10^{-3}$ mole) of pyridine were dissolved in 0.75 ml. of water (pH 6.5). The resulting solution was heated at 60° C for 6 hours, chromatographically purified by use of a resin column [Amberlite XAD-2, trade name of Rohm & Haas Co. USA, 16 × 700 mm., eluent: water, under the monitor of U.V. spectrometer (240 mμ)]. The fractions containing the desired cephalosporin are collected and then freeze-dried to to obtain 126 mg. of the desired product. IR $\nu_{max}^{KBr}$ (cm.$^{-1}$): 3400 (OH), 3020 (CH), 1760 (β-lactam), 1670 (—CONH—), 1610 (—COO-), 1525 (shoulder), 1490, 1380, 1350 ($SO_2$), 1220 ($SO_2$), 1037 (—$SO_2$—), 700 (no —SCN detected). NMR (60Mc, $D_2O$): 3.02, 3.48 (2H, doublet, $J_1$=$J_2$=18 c/s, $C_2$ methylene), 5.28, 5.40 (2H, 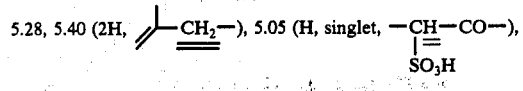—CH₂—), 5.05 (H, singlet, —CH—CO—),
|=
SO₃H 5.07 (1H, doublet, J=5.3 c/s, C₆ proton), 5.68 (1H, doublet, J=5.3 c/s, C₇ proton), 7.32, 7.45 (5H, phenyl proton), 7.8–9.0 (5H, multiplet, pyridine proton).

| Minimum inhibitory concentration: | | |
|---|---|---|
| *Pseudomonas aeruginosa* | (Pd 1) | 2 (μg./ml.) |
| " | (Pd 12) | 10 (μg./ml.) |
| " | (T-3) | 5 (μg./ml.) |
| " | (NCTC 10490) | 1 (μg./ml.) |
| " | (Pd 13) | 5 (μg./ml.) |
| *Staphylococcus aureus* | (209P) | 1 (μg./ml.) |
| " | (penicillin G resistant) | 2 (μg./ml.) |

EXAMPLE 2

0.292 Gram of N-(7-aminoceph-3-em-3-ylmethyl)pyridinium-4-carboxylate and 0.17 g. of sodium hydrogen-carbonate were dissolved in 7 ml. of water. Into the resulting solution was dropped under cooling 3 ml. of a chloroform solution containing 0.234 g. of α-sulfophenylacetyl chloride. After completion of the dropping, the stirring was further continued under cooling for 40 minutes to terminate the reaction. After removing the organic layer, the aqueous layer was adjusted to pH 6 and subjected to chromatography using Amberlite XAD-2, and the resulting desired product-containing fractions were freeze-dried to obtain sodium N-[7-(α-sulfophenylacetamido)ceph-3-em-3-ylmethyl]pyridinium-4-carboxylate.

EXAMPLE 3

Preparation of sodium N-[7-(α-sulfophenylacetamido)ceph-3-em-3-ylmethyl]-4'-carbamoyl-pyridinium-4-carboxylate 0.514 Gram (1 × 10⁻³ mole) of 7-(α-sulfophenylacetamido)cephalosporanic acid, 0.366 g. (3 × 10⁻³ mole) of isonicotinamide and 2.0 g. (2.06 × 10⁻² mole) of potassium thiocyanate were dissolved in 2.5 ml. of water. The resulting solution was allowed to stand and heated for 20 hours in a thermostat kept at 50° C, and then directly purified according to chromatography using an Amberlite XAD-2 column (16 × 880 mm.). Subsequently, cephalosporin-containing fractions were collected and subjected to freeze-drying to obtain 270 g. of the desired product in the form of pale yellowish white powder. IR $\nu_{max}^{KBr}$ (cm.⁻¹): 3330 (CH, NH), 3200 (OH, broad), 1765 (C=O, β-lactam), 1680 (—CONH—), 1610 (—COO⁻), 1552 (—NH₂, deformation), 1455, 1390 (C=C, SO₂), 1200 (SO₂, broad), 1120, 1040 (—SO₃⁻), 850, 810, 700. NMR (60Mc, D₂O):

2.93 (1H, doublet, J=18 c/s, 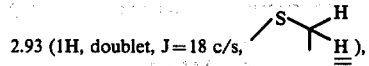), 3.52 (1H, doublet, J=18 c/s, 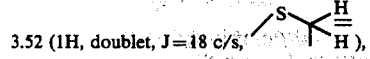),
5.08 (1H, singlet, —CH—),
|
SO₃

5.35 (1H, 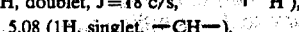—CH₂—), 5.50 (1H, doublet, J=5 c/s, 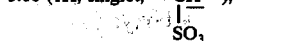—CH₂—), 5.09 (1H, doublet, J=6 c/s, 6-position proton), 5.71 (1H, doublet, J=4.5 c/s, 7-position proton), 7.25–7.6 (5H, multiplet, phenyl), 8.25 (2H, doublet, J=6.5 c/s, pyridine proton), 9.03 (2H, doublet, J=6.5 c/s, pyridine proton).

| Minimum inhibitory concentration: | | |
|---|---|---|
| *Pseudomonas aeruginosa* | (Pd 1) | 1 (μg./ml.) |
| " | (NCTC) | 0.5 (μg./ml.) |

EXAMPLE 4

Example 3 was repeated, except that each of quinoline, nicotinic acid, isonicotinic acid hydrazide, nicotinamide, isonicotinamide, 2-methylimidazole and isoquinoline was used in place of the isonicotinamide. The minimum inhibitory concentrations of the resulting compounds were as set forth in the following table:

| Substituent at the 3-position | MIC (μg./ml.) against *Pseudomonas aeruginosa* (Pd 12) |
|---|---|
| 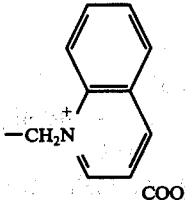 | 5 |
|  | 5 |
| 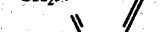 | 10 |
|  | 1 |
| 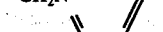 | 0.5 |
|  | 10 |
| 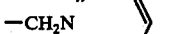 | 5 |

EXAMPLE 5

Preparation of sodium N-[7-(α-sulfophenylacetamido)-ceph-3-em-3-ylmethyl]-2'-methylpyridinium-4-carboxylate 0.355 Gram (0.9 × $10^{-4}$ mole) of disodium 7-(α-sulfophenylacetamido)cephalosporanic acid, 0.175 g. (1.88 × $10^{-3}$ mole) of α-picoline and 0.15 g. (1.55 × $10^{-3}$ mole) of potassium thiocyanate were dissolved in 0.8 ml. of water. The resulting solution was heated at 50° C for 20 hours and washed two times with 0.5 ml. each of methylene chloride. Thereafter, the aqueous layer was recovered, aded to an Amberlite XAD-2 column (16 × 900 mm.) and then chromatographically purified using water as a developer. Subsequently, cephalosporin-containing fractions were collected and subjected to freeze-drying to obtain 220 mg of the desired product in the form of pale yellowish powder. IR $\nu_{max}^{KBr}$ (cm.$^{-1}$): 3390 (OH), 3025 (CH), 1759 (β-lactam), 1670 (—CONH—), 1610 (COO), 1525 (C=C), 1490, 1450 (C=C), 1390–1340 ($SO_2$), 1220 ($SO_2$), 1038 ($SO_3$).

| Minimum inhibitory concentration: | | |
|---|---|---|
| *Pseudomonas aeruginosa* | (Pd 1) | 3 (μg./ml.) |
| " | (NCTC 10490) | 2 (μg./ml.) |

EXAMPLE 6

Preparation of sodium N-[7-(α-sulfopropionamido)ceph-3-em-3-ylmethyl]-pyridinium-4-Carboxylate 436 Milligrams (1 × $10^{-3}$ mole) of disodium 7-(α-sulfopropionamido)cephalosporante, 395 mg. (5 × $10^{-3}$ mole) of pyridine and 485 mg. (5 × $10^{-3}$ mole of KSCN were dissolved in 1.0 ml. of water, and the resulting solution was allowed to stand at 50° C for 5 hours. Subsequently, the reaction solution was purified according to column chromatography using Amberlite XAD-2 to obtain 70 mg. of the desired product. IR $\nu_{max}^{KBr}$ (cm.$^{-1}$): 1760 (β-lactam), 1670 (—CONH—), 1610 (—COONa), 1040 (—$SO_3$Na). NMR δ ($D_2O$): 1.58 (3H, doublet, J=6.5 c/s, $CH_3$—),

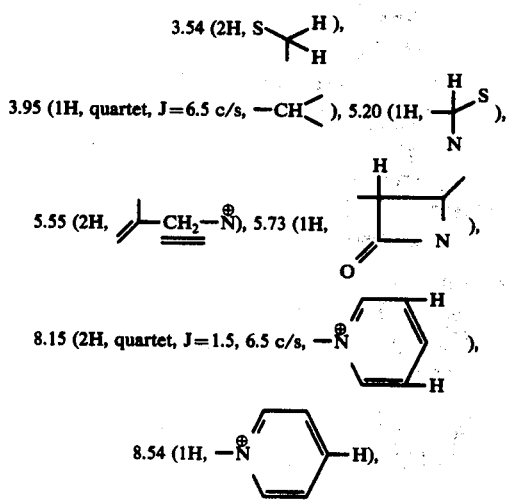

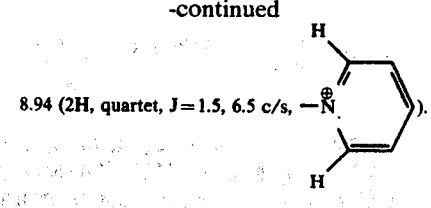

EXAMPLE 7

Preparation of sodium N-[7-(α-sulfocaproamido)ceph-3-em-3-ylmethyl]-pyridinium-4-carboxylate 450 Milligrams (1 × $10^{-8}$ mole) of disodium N-7-(α-sulfocaproamido)cephalosporanate, 395 mg. (5 × $10^{-3}$ mole) of pyridine and 485 mg. (5 × $10^{-3}$ mole) of KSCN were dissolved in 1.0 ml. of water, and the resulting solution was allowed to stand at 60° C for 5 hours. Subsequently, the reaction liquid was purified according to column chromatography using Amberlite XAD-2 to obtain 80 mg. of the desired product. IR $\nu_{max}^{KBr}$ (cm.$^{-1}$): 1763 (β-lactam), 1673 (—CONH—), 1613 (—COONa), 1038 (—$SO_3$Na). NMR δ ($D_2O$): 0.93 (3H, $CH_3$), 1.37 (4H, —($CH_2)_2$—),

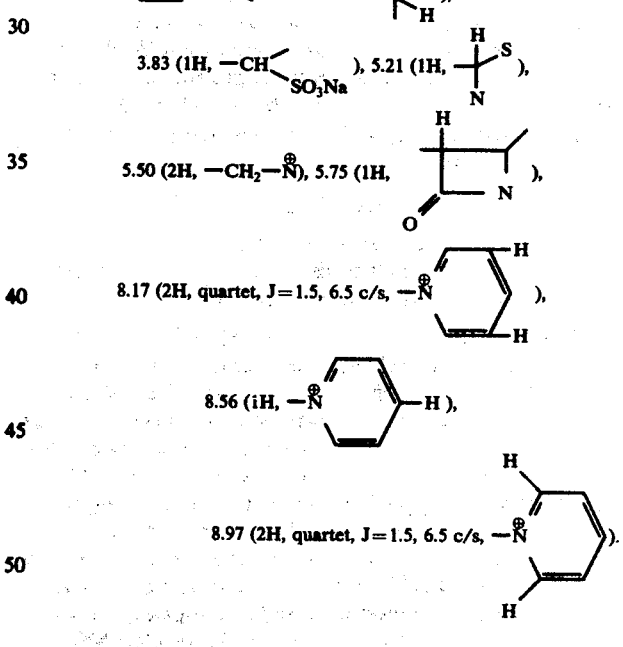

| Minimum inhibitory concentration: | | |
|---|---|---|
| *Staphylococcus aureus* | (No. 87, penicillin G resistant) | 2 (mcg./ml.) |
| *Pseudomonas aeruginosa* | (10490) | 2 (mcg./ml.) |

EXAMPLE 8

Preparation of sodium 7-sulfoacetamido-3-(pyridinium)-methylceph-3-em-4-carboxylate 638 Milligrams of disodium 7-sulfoacetamidocephalosporanic acid, 1.75 g. of KSCN and 240 mg. of pyridine were dissolved in 2 ml. of water, and the resulting solution was heated at 60° C for 7 hours. Subsequently, the reaction liquid was purified according to column chromatography using Amberlite XAD-2 to obtain 400 mg. of the desired product, yield 57%. IR $\nu_{max}^{KBr}$ (cm.$^{-1}$): 1766 ($\beta$-lactam), 1670 (—CONH—), 1620 (—CO$_2$-), 1550, 1485, 1395, 1370, 1330, 1210, 1047, (—SO$_3$-).

NMR $\delta$(D$_2$O):
3.30 (1H, doublet, J=18 c/s, S—CH<H,H>),
3.70 (1H, doublet, J=18 c/s, S—CH<H,H>),
3.92 (2H, CH$_2$—SO$_3$Na),
5.20 (1H, doublet, J=5 c/s, C$_6$—H),
5.80 (1H, doublet, J=5 c/s, C$_7$—H),
5.4, 5.7 (2H, AB$_q$, J=15 c/s, —CH$_2$—$\overset{+}{N}$),
7.9 – 9.2 (5H, multiplet, pyridine).

EXAMPLE 9

1. Preparation of $\alpha$-sulfo-$\alpha$-(p-nitrophenyl)acetic acid chloride 6.58 Grams (5.7 × 10$^{-2}$ M) of thionyl chloride, 2 ml. of ether and 2 drops of dimethylformamide were added to 1.5 g. (5.7 × 10$^{-3}$ M) of $\alpha$-sulfo-$\alpha$-(p-nitrophenyl)acetic acid to allow to react for 14.5 hours at room temperature. The reaction product was subjected to the evaporation to dryness under reduced pressure to obtain a crude desired product. Yield 81.3%.

NMR (60Mc, CDCl$_3$): 5.93 (CH, singlet), 8.06 (phenyl, quartet, J=8 c/s, J=14 c/s).

2. Preparation of disodium 7-[$\alpha$-sulfo-$\alpha$-(p-nitrophenyl)-acetamido]cephalosporanate 4.45 Milliliters of 1N-NaOH and 24 ml. of water were added to 1.2 g. (4.45 × 10$^{-3}$ M) of 7-aminocephalosporanic acid to prepare a solution. 0.87 Gram (1.04 × 10$^{-2}$ M) of NaHCO$_3$ was added to the solution under ice-cooling, and then a solution of 1.4 g. (4.45 × 10$^{-3}$ × 1.13 times M) of the crude $\alpha$-sulfo-$\alpha$-(p-nitrophenyl)acetic acid chloride obtained in (1) above in 8 ml. of acetone was slowly added over 10 minutes drop by drop thereto. Stirring was continued at 0°-2° C for 20 minutes and at 5° C for 1.5 hours, after the addition was completed. The solution was condensed up to 8 ml. under reduced pressure at room tempreature. The solution was passed through a column(6×100 cm.) packed with 1.81 of Amberlite XAD-2 resin and eluation was made with 8 ml. of water. Fractions nos. 1–15 obtained were freeze-dried to obtain 1.2 g. of the desired product.

IR $\nu_{max}^{KBr}$(cm.$^{-1}$): 3450 (—OH), 1760 (lactam), 1685 (acid amide), 1620 (carboxylate), 1520, 1350 (—NO$_2$), 1230, 1045 (—SO$_3$Na).

3. Preparation of sodium 7-[$\alpha$-sulfo-$\alpha$-(p-nitrophenyl)-acetamido]-3-(pyridiniummethyl)ceph-3-em-4-carboxylate 0.306 Milliliter (3.87 × 10$^{-3}$ M) of pyridine, 2.5 g. (2.58 × 10$^{-2}$ M) of KSCN and 1.2 ml. of water were added to 0.8 g. (1.43 × 10$^{-3}$ M) of disodium 7-[$\alpha$-sulfo-$\alpha$-(p-nitrophenyl)acetamido]cephalosporanate. The solution, after its pH was controlled at 6.5, was left to stand for 6 hours in a thermostat kept at 60° C, and over night under cooling.

4. Preparation of sodium 7-[$\alpha$-sulfo-$\alpha$-(p-aminophenyl)acetamido]-3-(pyridiniummethyl)ceph-3-em-4-carboxylate The solution obtained in (3) above was dissolved in 100 ml. of water and allowed to react for 50 minutes at 25° C under hydrogen initial pressure of 100 kg./cm.$^2$ in the presence of 1 g. of Raney nickel. Hydrogen absorption: 333%. The reaction solution was filtered and then the filtrate was condensed to 10 ml. under reduced pressure. The condensate was passed through a column (4.0 × 70 cm.) packed with 0.5 l. of Amberlite XAD-2 resin, and eluated with 1.6 l. of water. Fraction nos. 1–9 were freeze-dried to obtain the product captioned above.

IR $\nu_{max}^{KBr}$(cm.$^{-1}$): 3400 (—OH), 1760 (lactam), 1675 (acid amide), 1620 (—COONa), 1220, 1040 (—SO$_3$Na).

NMR (60Mc, D$_2$O): 2.03 (CH$_3$, 1H),

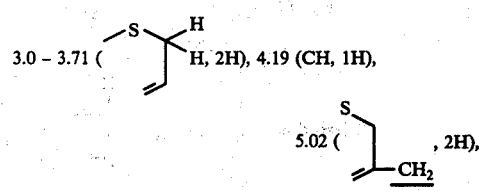

5.2–5.71 (6, 7-positioned H, 2H), 7.68 (phenyl, 4H), 8.8 (pyridine, 5H).

| Minimum inhibitory concentration: | |
|---|---|
| Staphylococcus aureus 209 P | 5 mcg./ml. |
| Pseudomonas aeruginosa | 5 mcg./ml. |

EXAMPLE 10

Preparation of sodium 7-($\alpha$-sulfo-$\alpha$-phenyl)acetamido-3-(p-acetaminopyridiniummethyl)ceph-3-em-4-carboxylate 200 Milligrams (3.87 × 10$^{-4}$ M) of disodium 7-($\alpha$-sulfo-$\alpha$-phenylacetamido)cephalosporanate, 120 mg. (8.82 × 10$^{-4}$ M) of 4-acetaminopyridine and 570 mg. (59 × 10$^{-3}$ M) of KSCN were mixed with 4 ml. of water, although some 4-acetaminopyridine was left undissolved. This solution containing some undissolved compound was allowed to react at 50° C for 18 hours in a glass vessel (8 ml.). After completion of the reaction, even the undissolved 4-acetaminopyridine was completely dissolved to obtain a transparent solution. The solution was purified by means of chromatography and freeze-dried to obtain 143 mg. of the product mentioned above. Yield: 60%.

IR $\nu_{max}^{KBr}$(cm$^{-1}$): 3500, 1760, 1720, 1670, 1510, 1455, 1360, 1315, 1225, 1200, 1040, 845, 700.

NMR (60Mc, D$_2$O): 2.308 (—NHCOCH$_3$).

EXAMPLE 11

Preparation of sodium 7-($\alpha$-sulfophenylacetamido)-3-[4'-methyl-5'-($\beta$-hydroxyethyl)thiazoliummethyl]ceph-3-em-4-carboxylate 500 Milligrams (9.69 × 10$^{-4}$ M) of disodium 7-($\alpha$-sulfo-$\alpha$-phenylacetamido)cephalosporanate, 1.68 g. (1.73 × 10$^{-3}$ M) of KSCN and 415 mg. (2.9 × 10$^{-3}$ M) of 4-methyl-5-($\beta$-hydroxyethyl) thiazole were dissolved in 2 ml. of water and allowed to react for 18 hours in a thermostat kept at 50° C. The solution thus obtained was subjected to chromatography using Amberlite XAD-2 resin and freeze-dried to obtain 264 mg. of the product captioned above. Yield: 42.8%.

IR $\nu_{max}^{KBr}$(cm.$^{-1}$): 3400, 3050, 1770, 1680, 1615, 1530, 1350, 1210, 1110, 1040, 700.

NMR (60Mc, D$_2$O):

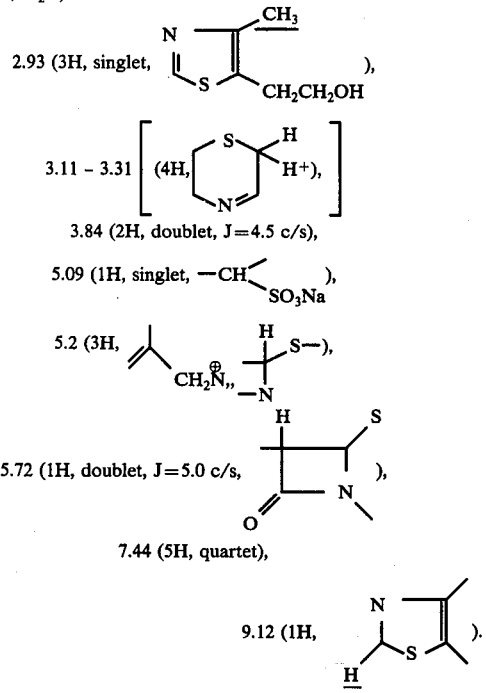

2.93 (3H, singlet, [structure]), 3.11 – 3.31 (4H, [structure]), 3.84 (2H, doublet, J=4.5 c/s), 5.09 (1H, singlet, —CH$\stackrel{\textstyle{}}{\text{SO}_3\text{Na}}$), 5.2 (3H, [structure]), 5.72 (1H, doublet, J=5.0 c/s, [structure]), 7.44 (5H, quartet), 9.12 (1H, [structure]).

EXAMPLE 12

514 Milligrams of disodium N-7-(α-sulfophenyl-acetamido)cephalosporanate and 1.2 g. of KSCN were dissolved in 1.5 ml. of water and to the solution was added 1.58 g. of 3-bromo-pyridine. A small amount of dimethylformamide was added to the mixture, then the resulting solution was left standing at 60° C for 10 hours. Subsequently, the reaction solution was purified according to column chromatography using Amberlite XAD-2. The desired product-containing fractions were freeze-dried to obtain sodium N-[7-(α-sulfo-phenylacetamido)ceph-3-em-3-(3′-bromopyridinium)-methyl]-4-carboxylate.

IR $\nu_{max}^{KBr}$ (cm.$^{-1}$): 1778 shoulder, 1765 ($\beta$-lactam), 1725 shoulder, 1670 (—CONH—), 1615 (—CO$_2$$^-$), 1210, 1038 (—SO$_3$$^-$).

NMR ≃ (D$_2$O): 3.5 (2H, broad, C—2), 5.17 (1H, C$_6$-H), 5.26 (1H, S, —CH<), 5.4 (2H, [structure]—CH$_2$—), 5.72 (1H, C$_7$—H),
7.6 (5H, phenyl), 8.0 (1H, [structure]), 8.7 – 9.1 (2H, [structure]),

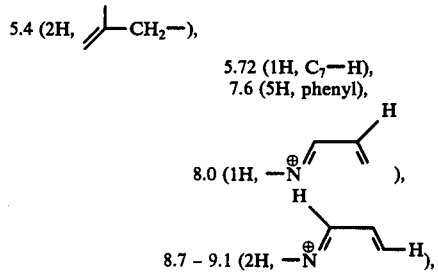

9.33 (1H, [structure]).

EXAMPLE 13

1. With cooling and stirring, 1.84 g. (0.0068 mole) of 7-ACA was suspended in 25 ml. of water and to the suspension was added dropwise 6.8 ml. of a 1N-aqueous solution of sodium hydroxide to dissolve 7-ACA. On the other hand, to a suspension of 1.5 g. (0.0068 mole) of α-sulfo-3-thienylacetic acid in 10 ml. of ether were added 5.5 ml. of thionyl chloride dropwise and 3 drops of dimethylformamide, then the resulting solution was stirred for 5 hours at room temperature. The reaction solution was subjected to the evaporation to dryness under reduced pressure to give α-sulfo-3-thienylacetyl chloride as a residue. The residue was dissolved in 10 ml. of ethyl acetate and the solution was added dropwise to the 7-ACA solution mentioned above, followed by stirring for 30 minutes. The aqueous layer was separated from the reaction solution and adjusted it pH to 6.5 by adding a saturated aqueous solution of NaHCO$_3$. The resulting solution was freeze-dried to obtain 3.6 g. of a crude product. The product was purified according to column chromatography using Amberlite XAD-2 to obtain 1.6 g. (42%) of 7-(α-sulfo-3′-thienylacetamido)-cephalosporanic acid.

IR $\nu_{max}^{KBr}$ (cm.$^{-1}$): 1750 ($\beta$-lactam, —OCOCH$_3$), 1677 (—CONH—), 1605 (—COONa), 1225 (—SO$_3$Na, —OAC), 1043 (SO$_3$Na).

NMR ≃ (D$_2$O): 2.13 (3H, singlet, —CO$_2$CH$_3$), 3.54 (2H, broad, [structure]), 5.10 (1H, doublet, J=4.7 c/s, [structure]), 5.24 (1H, singlet, —CH< ), 5.70 (1H, doublet, J=4.7 c/s, [structure]), 7.38 – 7.67 (3H, multiplet, 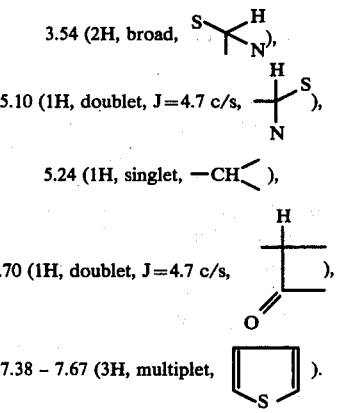).

2. 260 Milligrams (0.5 × 10$^{-3}$ mole) of 7-(α-sulfo-3-thienylacetamido)cephalosporanic acid and 97 mg. (1 × 10$^{-3}$ mole) of KSCN were added to a solution of 240 mg. (3 × 10$^{-3}$ mole) of pyridine dissolved in 2 ml. of water, and the resulting solution left standing for 24 hours at 40° C. The reaction mixture was washed with ether. The aqueous layer separated was purified according to column chromatography using Amberlite XAD-2 to obtain sodium N-[7-(α-sulfo-3-thienylacetamido)-ceph-3-em-3-ylmethyl]-pyridinium-4-carboxylate.

Minimum inhibitory concentration:
Pseudomonas aeruginosa (Pd 1) 2 (μg./ml.)
" (NCTC 10490) 1 (μg./ml.)

IR $\nu_{max}^{KBr}$ (cm.$^{-1}$): 1764 ($\beta$-lactam), 1675 (—CONH—), 1614 (—CO$_2$Na)

NMR $\delta$(D$_2$O):

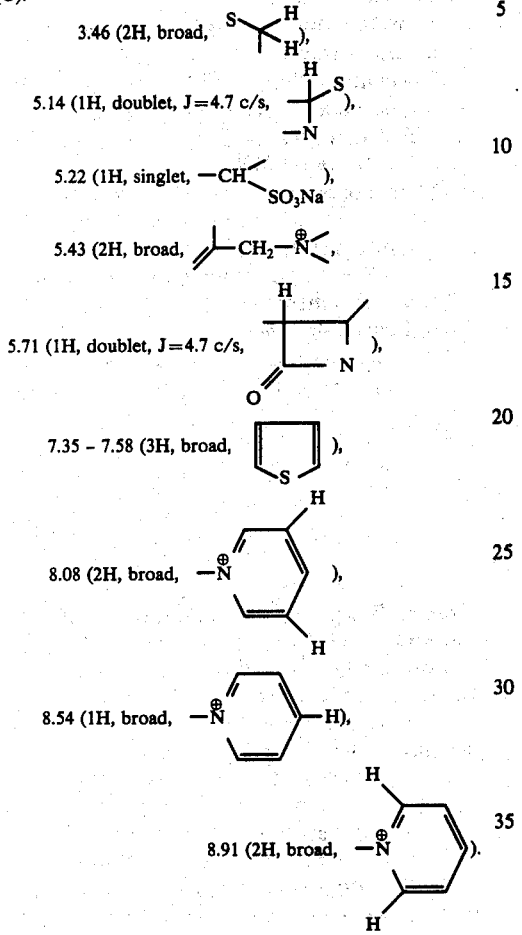

3.46 (2H, broad, S\\C(H,H)), 5.14 (1H, doublet, J=4.7 c/s, ), 5.22 (1H, singlet, —CH\\SO$_3$Na), 5.43 (2H, broad, =\\CH$_2$—N⊕\\), 5.71 (1H, doublet, J=4.7 c/s, ), 7.35 – 7.58 (3H, broad, thiophene), 8.08 (2H, broad, —N⊕ ), 8.54 (1H, broad, —N⊕—H), 8.91 (2H, broad, —N⊕ ).

EXAMPLE 14

A mixture of 1.5 ml. of dimethylformamide, 1 ml. of water and 307 mg. (2.5 × 10$^{-3}$ mole) of pyrazineamide was heated at 50° C to obtain a uniform solution. The solution was added to a solution of 260 mg. (0.5 × 10$^{-3}$ mole) of 7-($\alpha$-sulfo-3-thienylacetamido)cephalosporanic acid and 97 mg. (1 × 10$^{-3}$ mole) of KSCN dissolved in 1 ml. of water. The mixed solution was allowed to stand at 45° C for 24 hours, followed by cooling. The precipitated crystals was filtered off and the filtrate was purified according to column chromatography using Amberlite XAD-2 to give sodium 7-($\alpha$-sulfo-3'-thienylacetamido)ceph-3-em-3(3''-carbamoyl-pyrazinium)methyl-4-carboxylate.

IR $\nu_{max}^{KBr}$ (cm.$^{-1}$): 1757 ($\beta$-lactam), 1660 (—CONH—, —CONH$_2$), 1615 (—COONa), 1040 (—SO$_3$Na).

EXAMPLE 15

213 Milligram (2.5 × 10$^{-3}$ mole) of thiazole, 97 mg. (1 × 10$^{-3}$ mole) of KSCN and 260 mg (0.5 × 10$^{-3}$ mole) of 7-($\alpha$-sulfo-3-thienylacetamido)cephalosporanic acid were dissolved completely in 0.8 ml. of water. The solution was left standing at 50° C for 20 hours and then purified according to column chromatography using Amberlite XAD-2 to obtain 80 mg. of sodium N-[7-($\alpha$-sulfo-3'-thienylacetamido)ceph-3-em-3-ylmethyl]-thiazolium-4-carboxylate.

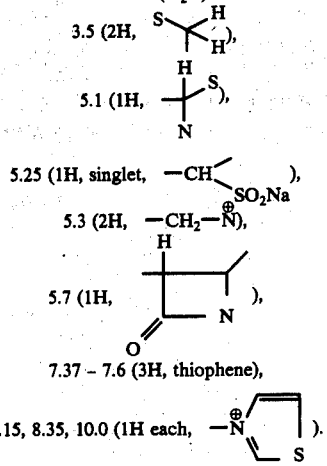

IR$\nu_{max}^{KBr}$(cm.$^{-1}$):
1757 ($\beta$-lactam), 1670 (—CONH—,—N⊕=C),
1617 (—COONa),
1038 (—SO$_3$Na)

NMR $\delta$(D$_2$O):

3.5 (2H, S\\C(H,H)), 5.1 (1H, ), 5.25 (1H, singlet, —CH\\SO$_2$Na), 5.3 (2H, —CH$_2$—N⊕), 5.7 (1H, ), 7.37 – 7.6 (3H, thiophene), 8.15, 8.35, 10.0 (1H each, —N⊕\\S ).

EXAMPLE 16

408 Milligrams (3 × 10$^{-3}$ mole) of 4-acetamino-pyridine, 485 mg. (5 × 10$^{-3}$ mole) of KSCN and 260 mg. (0.5 × 10$^{-3}$ mole) of 7-($\alpha$-sulfo-3-thienylacetamido)-cephalosporanic acid were dissolved in 1 ml. of water and the solution was left standing at 50° C for 10 hours. The reaction solution was purified according to column chromatography using Amberlite XAD-2 to obtain sodium N-[7-($\alpha$-sulfo-3-thienylacetamido)ceph-3-em-3-ylmethyl]-4'-acetamido-pyridinium-4-carboxylate.

IR $\nu_{max}^{KBr}$ (cm.$^{-1}$): 1760 ($\beta$-lactam), 1670 (—CONH—, —NH—COCH$_3$), 1610 (—COONa), 1040 (—SO$_3$Na).

NMR $\delta$ (D$_2$O):

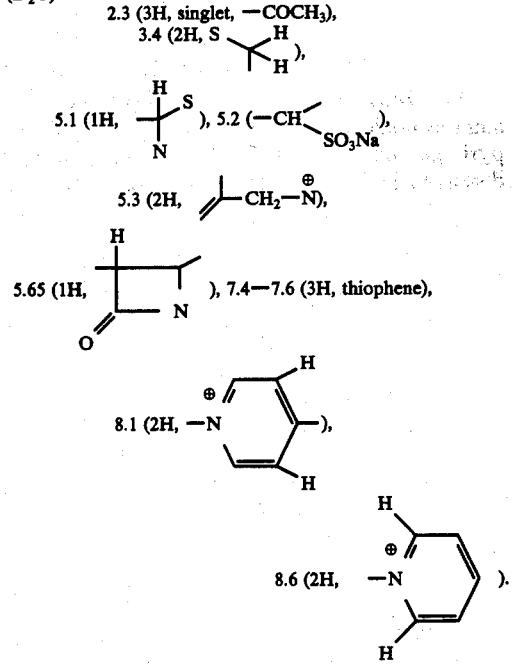

2.3 (3H, singlet, —COCH$_3$),
3.4 (2H, S\\C(H,H)), 5.1 (1H, ), 5.2 (—CH\\SO$_3$Na), 5.3 (2H, =\\CH$_2$—N⊕), 5.65 (1H, ), 7.4—7.6 (3H, thiophene), 8.1 (2H, —N⊕ ), 8.6 (2H, —N⊕ ).

EXAMPLE 17

420 Milligrams (3 × 10⁻³ mole) of 4-β-hydroxyethyl-5-methylthiazole, 485 mg. (5 × 10⁻³ mole) of KSCN and 260 mg. (0.5 × 10⁻³ mole) of 7-(α-sulfo-3-thienylacetamido)-cephalosporanic acid were dissolved in 1 ml. of water and thus obtained solution was allowed to stand at 50° C for 10 hours. The reaction solution was purified according to column chromatography using Amberlite XAD-2 to obtain sodium N-[7-(α-sulfo-3'-thienylacetamido)ceph-3-em-3-ylmethyl]-4''-β-hydroxyethyl-5''-methyl-thiazolium-4-carboxylate.

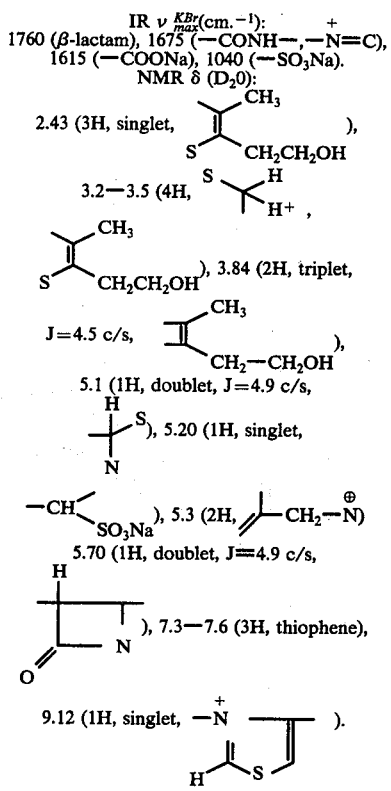

EXAMPLE 18

558 Milligrams (2 × 10⁻³ mole) of sodium 7-aminocephalosporanate, 790 mg. (1 × 10⁻³ mole) of pyridine and 1.94 g. (2 × 10⁻³ mole) of KSCN were dissolved in 2 ml. of water and the resulting solution was left standing at 50° C for 8 hours. The reaction solution was purified according to column chromatography using Amberlite XAD-2 to obtain pyridinium 7-aminocephalosporanate, which was dissolved in 10 ml. of water and the solution was reacted with 235 mg. of α-sulfo-3-thienylacetyl chloride to obtain sodium N-[7-(α-sulfo-3'-thienylacetamido)ceph-3-em-3-ylmethyl]pyridinium-4-carboxylate. This compound was identified with the product obtained in Example 13 by means of IR and NMR.

Other representative compounds which may be produced in accordance with the present invention are 7-(α-sulfo-p-nitrophenylacetamido)ceph-3-em-3-ylmethyl-2'-methylpyridinium-4-carboxylate and 7-(α-sulfo-p-aminophenylacetamido)ceph-3-em-3-ylmethyl-2'-methylpyridinium-4-carboxylate.

What we claim is:

1. A compound of the formula:

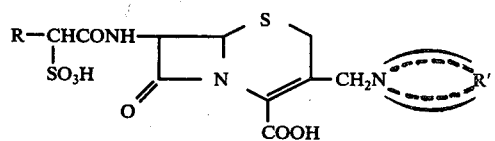

wherein R is phenyl or thienyl, and R' is a group which constitutes together with the adjacent nitrogen atom a pyridinium group, said pyridinium group being substituted by carbamoyl at the 4'-position, or a 4'-methyl-5'-(β-hydroxyethyl)-thiazolium or a pharmaceutically acceptable salt thereof.

2. The compound of claim 1, wherein R is phenyl and R' is a group which constitutes together with the adjacent nitrogen atom a pyridinium group that is substituted with carbamoyl at the 4' position.

3. The compound of claim 1, namely N-[7-(α-sulfophenylacetamido)ceph-3-em-3-ylmethyl]-4'-carbamoylpyridinium-4-carboxylic acid.

4. The compound of claim 1, namely 7-(α-sulfophenylacetamido)-3-[4'-methyl-5'-(β-hydroxyethyl)-thiazolium-methyl]ceph-3-em-4-carboxylic acid.

5. The compound of claim 1, namely sodium N-[7-(α-sulfophenylacetamido)ceph-3-em-3-ylmethyl]-4'-carbamoylpyridinium-4-carboxylate.

6. The compound of claim 1, namely sodium 7-(α-sulfophenylacetamido)-3-[4'-methyl-5'-(β-hydroxyethyl)-thiazolium-methyl]ceph-3-em-4-carboxylate.

* * * * *